US008894577B2

(12) United States Patent
Reed et al.

(10) Patent No.: US 8,894,577 B2
(45) Date of Patent: *Nov. 25, 2014

(54) SYSTEM AND METHOD FOR MEDICAL INFORMATION MONITORING AND PROCESSING

(75) Inventors: William C. Reed, Portland, OR (US); Lydia Lundberg, Portland, OR (US); William (Bill) Pascoe, Rainier, OR (US); Shannon Lundberg, Portland, OR (US)

(73) Assignee: Elite Care Technologies, Inc., Portland, OR (US)

( * ) Notice: Subject to any disclaimer, the term of this patent is extended or adjusted under 35 U.S.C. 154(b) by 1438 days.
This patent is subject to a terminal disclaimer.

(21) Appl. No.: 11/292,216

(22) Filed: Nov. 30, 2005

(65) Prior Publication Data
US 2006/0084847 A1 Apr. 20, 2006

Related U.S. Application Data

(60) Continuation-in-part of application No. 10/997,622, filed on Nov. 23, 2004, now Pat. No. 7,001,334, which is a continuation of application No. 10/358,458, filed on Feb. 4, 2003, now Pat. No. 6,821,258, which is a division of application No. 09/706,327, filed on Nov. 3, 2000, now Pat. No. 6,524,239.

(60) Provisional application No. 60/163,709, filed on Nov. 5, 1999.

(51) Int. Cl.
*A61B 5/00* (2006.01)
*G06Q 10/00* (2012.01)
(Continued)

(52) U.S. Cl.
CPC ............... *G06F 19/32* (2013.01); *G06F 19/34* (2013.01); *G06F 15/173* (2013.01);
(Continued)

(58) Field of Classification Search
CPC ..... G06F 19/30–19/366; G06F 21/62–21/629; G06F 17/30–17/30064; G08B 21/02–21/0211; G08B 21/0269–21/0272; A61B 5/0002; A61B 5/1112–5/1113; A61B 2505/00–2505/09
USPC ..................... 600/300, 301; 705/2, 3; 707/10, 707/781–784; 709/203; 340/573.1, 870.01, 340/539.12, 539.13; 128/903–905, 920
See application file for complete search history.

(56) References Cited

U.S. PATENT DOCUMENTS 5,343,869 A 9/1994 Pross et al.
5,410,471 A 4/1995 Alyfuku et al.
(Continued)

OTHER PUBLICATIONS

Stanford, "Using Pervasive Computing to Deliver Elder Care," *Pervasive Computing*, vol. 1, No. 1 (Jan.-Mar. 2002).
(Continued)

*Primary Examiner* — William Thomson
*Assistant Examiner* — Marie Archer
(74) *Attorney, Agent, or Firm* — Marger Johnson & McCollom, PC

(57) ABSTRACT

A method of monitoring health parameters of subjects within a defined space and over a period of time includes collecting first data corresponding to a physiological parameter of an ambulatory subject, collecting second data corresponding to a behavioral and cognitive parameter of the ambulatory subject, collecting third data corresponding to an identity and a location of the one of the subjects, collecting fourth data corresponding to the one of the ambulatory subjects from third party sources, generating a data record for the one of the ambulatory subjects based upon the first, second, third, and fourth data, and outputting a modified data record, the modified data record containing portions of the data record, the portions selected based upon an access level of a person requesting the data record and a format of the modified data record selected based upon the access level and community needs.

16 Claims, 3 Drawing Sheets

(51) Int. Cl.
  *G06F 11/00* (2006.01)
  *G08B 13/14* (2006.01)
  *A61B 5/103* (2006.01)
  *G06F 15/173* (2006.01)
  *G06F 21/62* (2013.01)
  *G08B 21/02* (2006.01)
  *A61B 5/11* (2006.01)
  *G06F 19/00* (2011.01)
  *G06F 15/16* (2006.01)
  *G08B 21/00* (2006.01)

(52) U.S. Cl.
  CPC ....... *G06F 21/6245* (2013.01); *G08B 21/0211* (2013.01); *A61B 5/747* (2013.01); *A61B 5/0002* (2013.01); *A61B 5/1112* (2013.01); *A61B 5/1113* (2013.01); *A61B 2505/07* (2013.01)
  USPC ............ 600/301; 705/2; 705/3; 702/188; 600/595; 340/570; 340/870.01; 340/539.12; 340/539.13; 707/781; 707/782; 707/783; 707/784

(56) References Cited

U.S. PATENT DOCUMENTS

| | | | | |
|---|---|---|---|---|
| 5,458,123 A | * | 10/1995 | Unger | 600/509 |
| 5,571,973 A | | 11/1996 | Taylot | |
| 5,692,215 A | | 11/1997 | Kutzik et al. | 395/838 |
| 5,780,798 A | | 7/1998 | Hall-Jackson | |
| 5,838,237 A | * | 11/1998 | Revell et al. | 340/573.1 |
| 5,844,488 A | | 12/1998 | Musick | |
| 5,950,632 A | | 9/1999 | Reber et al. | |
| 5,959,529 A | * | 9/1999 | Kail, IV | 340/539.12 |
| 6,050,940 A | | 4/2000 | Braun et al. | |
| 6,073,046 A | | 6/2000 | Patel et al. | |
| 6,076,166 A | * | 6/2000 | Moshfeghi et al. | 726/4 |
| 6,113,539 A | | 9/2000 | Ridenour | |
| 6,155,120 A | | 12/2000 | Taylor | |
| 6,163,903 A | | 12/2000 | Weismiller et al. | |
| 6,198,394 B1 | * | 3/2001 | Jacobsen et al. | 340/573.1 |
| 6,290,646 B1 | | 9/2001 | Cosentino et al. | |
| 6,302,844 B1 | * | 10/2001 | Walker et al. | 600/300 |
| 6,468,234 B1 | | 10/2002 | Van Der Loos et al. | |
| 6,471,087 B1 | * | 10/2002 | Shusterman | 221/2 |
| 6,546,813 B2 | | 4/2003 | Hubbard | |
| 6,611,206 B2 | | 8/2003 | Eshelman et al. | |
| 6,684,418 B2 | | 2/2004 | Choi | |
| 6,699,195 B2 | | 3/2004 | Nakazawa et al. | |
| 6,723,040 B2 | | 4/2004 | Brady | |
| 6,802,808 B2 | | 10/2004 | Brady | |
| 6,980,958 B1 | | 12/2005 | Surwit et al. | |
| 2003/0036683 A1 | * | 2/2003 | Kehr et al. | 600/300 |
| 2004/0122489 A1 | * | 6/2004 | Mazar et al. | 607/60 |

OTHER PUBLICATIONS

Moody, "Oatfield Estates, Assisted Living Community Offers New Options," *The Business Journal*, vol. 19, No. 50 (Feb. 7, 2003).
Macht, "Estate Aged," *Urban Land* (Oct. 2001).
Edwards, "Striving to Achieve, Aging in Place," *Nursing Homes, Long Term Care Management*, vol. 51, No. 2 (Feb. 2002).
Barnett, "House Wire, An Assisted-living Center Goes High-tech to Care for Its Residents," *The Oregonian*, TechNW (Jun. 26, 2000).
Fox, "Technogenarians," *Wired*(Nov. 2001).
Shellenbarger, "Technology Holds Promise for Easing Families' Worries Over the Elderly," *The Wall Street Journal*, Personal Journal (Jul. 25, 2002).
Shellenbarger, "The Brave New World for Eldercare, Gadgets Track Loved One's Every Move," *The Wall Street Journal*, Personal Journal (Jul. 18, 2002).
Donahue, "Byte, Byte, Against the Dying of the Light," *The Atlantic Monthly* (May 2001).
Johnston, "Oatfield Estates, A Senior Community Profile," *The Oregonian*, Homes & Real Estate (Sep. 16, 2001).
Gelhaus, "High-Tech Homes, Mean A Brighter Future For Seniors," *Provider* (Sep. 2002).

* cited by examiner

SYSTEM AND METHOD FOR MEDICAL INFORMATION MONITORING AND PROCESSING

CROSS-REFERENCE TO RELATED APPLICATIONS

This application is a continuation-in-part of prior Application No. 10/997,622, filed on 23 Nov. 2004, now U.S. Pat. No. 7,001,334, which is a continuation of prior Application No. 10/358,458, filed on 4 Feb. 2003, now U.S. Pat. No. 6,821,258, which is a divisional of prior Application No. 09/706,327, filed on 3 Nov. 2000, now U.S. Pat. No. 6,524,239, which claims the benefit of U.S. Provisional Application No. 60/163,709, filed on 5 Nov. 1999. The related applications specified above are incorporated by reference in their entirety.

BACKGROUND

1. Technical Field

This disclosure relates generally to a health monitoring apparatus, and more specifically to a system method for medical information mining and delivery.

2. Description of the Related Art

A subject's health status is typically evaluated by reference to a plurality of vital signs that may include, for example, pulse rate, respiration rate, temperature, blood oxygen saturation, weight, and body hydration. Additional considerations include observations as to subject appearance and movement. These latter factors are also indicative of the subject's mental health, e.g., cognitive ability. Other cues are the degree of animation, compliance with responsibilities such as self-medication, forgetfulness, socialization, participation in individual or group activities, and the like.

In traditional long term care facilities, these indices are measured and observed by caregivers. While measurements are sometimes recorded, only a small portion of the observations are retained in the institution's memory. This fact is especially true in the case of cognitive health cues.

Care giving personnel serve the critical role of observing and preserving the meaning and functionality of health data. Interacting with a patient over a period of time, a caregiver learns a great deal about the habits and individual health trends of that patient. The large volumes of observed data provide evidence to support the diagnostics of health care professionals. Raw data pertaining to a subject's health status provides the context in which present parameter values can be assessed.

With the frequent turnover of caregivers, this context is minimized or lost unless the observed information has been reduced to writing for the new personnel. Typically, only a small fraction of the total observed data is recorded. Sub-clinical observations are frequently useful in assessing the subject's health status, especially cognitive abilities. These data include the subject's demeanor, alertness, regularity, and mobility. The common denominator is that these characteristics change gradually. They are therefore less noticeable to new personnel, who have not observed the subject over time and are not familiar with these characteristics.

Caregiver turnover is in part a result of the constant pressure care givers are under to record and understand the daily routines of the subjects. By tailoring the information acquisition and feed back to their personal abilities and needs this pressure is reduced and they are able to experience more job satisfaction, thus reducing turnover.

Short institutional memory produces a lengthening of the time before caregivers or other health professionals become cognizant of a slow decline in a subject's health status. The delay in appreciating a decline causes a corresponding delay in responding to the health deterioration of the subject. As a result, the quality of health care received by a subject may be degraded.

Embodiments of the invention address these and other disadvantages of the conventional art.

DETAILED DESCRIPTION

Figure 1:
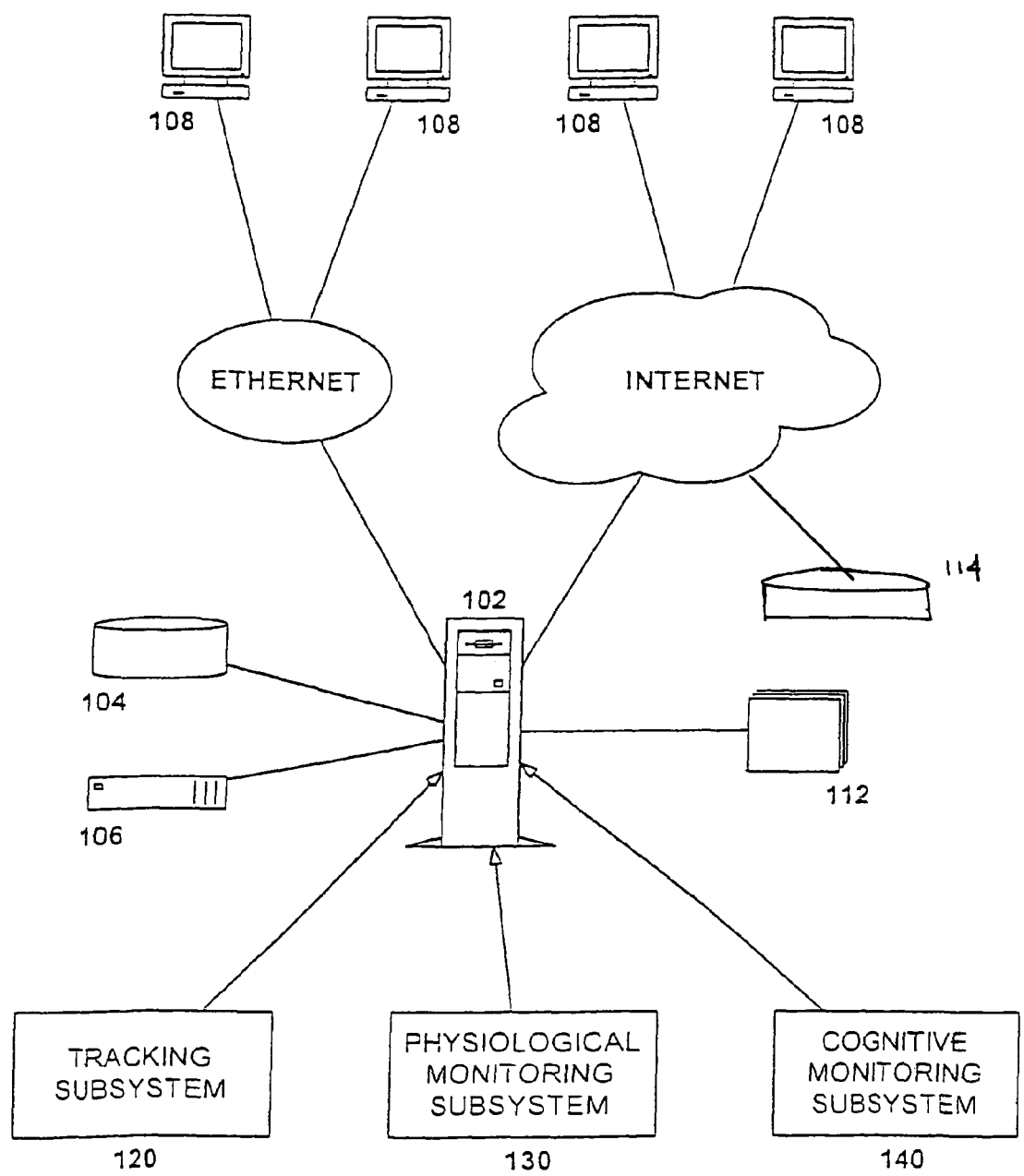
FIG. 1 is a block diagram of a system according to some embodiments of the invention.

According to some embodiments of the invention, an integrated subject monitoring system facilitates measurement, collection, and analysis of objective and subjective data pertaining to the physiological and behavioral health status of a subject.

According to some embodiments, the system can collect objective and subjective data pertaining to the physiological and behavioral health status of the subject and combine this data with other data that was collected or compiled by sources other than the system to create a more comprehensive picture of the status of a subject. These other sources will be referred to as third party sources. The data collected by the system may include information that is manually entered into the system by a user of the system. The data collected or compiled by third party sources could include, but are not limited to, medical records, pharmacy records, medical information services, and other web based information.

According to some embodiments, the system includes a network with a computer, data storage device and data analysis means. Raw data and analyses can thereby be accessed by the subject or resident caregiver. Additionally, this information is web based and can be remotely accessed by a health care provider, family member or other authorized entity.

Some embodiments include subsystems that are operative to obtain measurements of a subject's physiological or behavioral/cognitive parameters within a defined multi-room space. Parameter data is measured primarily passively and without the intentional cooperation of the subject. Accordingly, the majority of the health parameter data can be obtained without relying upon the subject to remember or to actively participate in data acquisition.

According to some embodiments, the system provides for prompts to be given a subject, to promote activities such as medication compliance, continence, and interactive parameter measurement. These prompts serve both to increase compliance as well as to encourage and reinforce routine behaviors and activities, creating a sense of well being.

In some embodiments, the system includes a subsystem to monitor subject location within the defined space and the curtilage thereof. This monitoring is performed without direct human supervision. Upon the request of a user, the system provides real-time information concerning the location of a monitored subject. Analyzed as a function of time, positional measurements provide locomotive information about the subject.

Furthermore, according to some embodiments control of ambient/environmental conditions is affected through the system. Environmental inputs by a subject are recorded, enabling a system user to assess physical as well as cognitive aspects of the subject.

According to other embodiments, a method of monitoring the physiological and behavioral/cognitive health status of an ambulatory subject is provided where monitoring is primarily accomplished passively and without the active cooperation of the subject. Indicia of physical and mental health may be monitored by the system. An initial baseline may be established for each of the measured parameters. Subject parameters may be continuously sampled and recorded. Each reading may be compared to the baseline as well as to the trend for the parameter of that subject. A user may input parameter boundaries, which then serve as predetermined thresholds for that parameter. When a reading falls outside the boundaries, the system may trigger a tailored message that reinforces the overall goals of the system to the appropriate party.

Using chronological identifiers, the system may also determine physical or behavioral anomalies as a function of time. A user can set the system to transmit an alert when two or more parameter deviations occur contemporaneously. Thus, the system can be instructed that a combination of discrete deviations is of sufficient concern that warning message is merited, even when any one of the deviations would not trigger a warning.

As used herein, certain terms are meant to convey specific meanings. In the taking of a measurement by a sensor, "passive" or "irrespective of subject cooperation" means that the parameter measurement occurs without conscious collaboration on the part of the subject to accomplish a measurement.

Lack of cooperation means that, for those health parameters measured passively, the subject need not even be aware that a sensor is present or that a measurement is being taken.

The term "ambulatory" means that the subject is capable of perambulation without personal assistance; i.e., the subject is not bedridden.

A cognitive parameter is a parameter that is indicative of the mental process or faculty of a subject, including abilities such as awareness, perception, reasoning, memory and judgment. A behavioral parameter refers to an indication in the form of an action of a subject, as well as a reaction in response to an external or internal stimulus. As used hereinafter, the term "cognitive" encompasses both cognitive as well as behavioral cues.

FIG. 1 is a block diagram illustrating a health monitoring system that is operative to monitor physiological and behavioral/cognitive indices of a subject according to some embodiments of the invention.

As shown in FIG. 1, the system includes a computer 102 that is coupled to a network, such as the qainternet or an Ethernet, the network being accessible by at least one remote node 108. The computer is further coupled to a tracking subsystem 120, a physiological monitoring subsystem 130, and a cognitive monitoring subsystem 140, which are described in further detail below.

The system further includes a computer 102, a data storage device 104, and a data analysis means 106. It will be recognized by those of skill in the art that although the data storage device 104 and the data analysis means 106 are illustrated as being separate from the computer 102, in other embodiments of the invention the data storage device and data analysis means may form part of the computer 102.

The computer 102 may be programmed to collect information in the form of measurements, associate Subject Identification Codes (SICs) therewith, further associate chronological identifiers (i.e., a time stamp) where appropriate, and generate a data record based upon the collected information, SICs, and chronological identifiers.

The collected measurement data and the data record may be stored in the data storage device 104. The data analysis means 106 is used to analyze the stored data records and tailor messages to the appropriate party in a user-friendly format that reinforces the overall goals of the system. According to some embodiments of the invention, the data analysis means 106 may constitute, for example, a processor.

According to some embodiments of the invention, the processor 106 is configured to detect a negative trend in a quality of service to one of the subjects. Furthermore, the processor 106 may issue a system alert when the detected negative trend exceeds a predetermined threshold value. The issue system alert may be sent to one or more of the remote network nodes 108.

The types of analyses that may be performed by the processor or data analysis means 106 are discussed in further detail below.

As shown in FIG. 1, a third party information source 114 may be coupled to the internet. According to some embodiments of the invention, the computer 102 may include a search engine that is capable of searching for and collecting information about a subject that exists on the third party information source 114. The information from the third party information source 114 may be used in addition to the information that is collected by the subsystems 120, 130, 140 to generate the data record.

System outputs may include health status and care reports 110 and billing summaries 112. These reports can be delivered via conventional methods (e.g., printed and mailed) or accessed via remote network nodes 108 that are connected to the computer 102 via the Internet or an ethernet.

Caregivers are responsible for recording, via the remote network nodes 108, the types of services provided to each subject. In traditional residential care settings, caregivers take hand-written notes. According to embodiments of the invention, examples of remote network nodes 108 may include a touch screen, a palmtop digital assistant, a keyboard, voice recognition or other input device. This computerized process decreases the amount of time caregivers spend writing down notes and maximizes the time that can be devoted to providing care services.

As needed, a caregiver may also input general observations pertaining to a subject. A subject may also enter comments and non-observable complaints and symptoms. These comments are entered into one of a plurality of internet or intranet terminals 108 that are distributed throughout the defined space. The terminals can also have voice recognition software or optical character recognition scanners so that caregivers can enter information without typing. A person skilled in the art will also recognize other ways of entering information into the system.

As with other measurements, data that is entered is associated with a chronological identifier and stored. This data point can be used in care giving assessments as well as summaries 112. Summaries can include billing statements, care reports and other matters, which are generated and distributed either online or through traditional avenues as each of these reports may be tailored to the person using the information.

According to some embodiments of the invention, subject location and movement, physiological, and cognitive parameters may be monitored by subsystems. These subsystems gather data from which the health status of the subject can be determined. The data-gathering sensors report information to the system, which then identifies the measured subject using the tracking subsystem data. The system thereby can associate a SIC and a chronological identifier to the parameter datum.

A first monitoring subsystem is a tracking subsystem 120, useful to monitor the location and mobility of a subject. Each subject carries a small radio frequency (RF), infrared (IR), or other wireless personal transmitter that is operable to transmit a code unique to that subject. A subset of the sensors is RF-, IR-, or other wireless receivers, distributed throughout the defined space and its curtilage. As the subject moves about in this region, sensors detect subject presence and signal the system of the subject's location.

The wireless personal transmitters may act as identification badges and serve as keys to gain access to certain rooms. Each personal transmitter may also include a "panic button", which enables the subject to issue an emergency call to the system in the event immediate attention is required. Once activated, the personal transmitter notifies the system of both the identity and exact location within the facility of the subject. This information shortens reaction time and permits a customized response.

By associating chronological identifiers to these signals, the system can calculate locomotion data that is informative of a subject's mobility, e.g., walking speed. This data can be used in conjunction with other health data to determine health problems and act as an early warning system to future health declines. Further, overall distance traveled can be assessed, both to evaluate the level of the subject's activity and exercise as well as to detect any decline in locomotive ability or health.

If a subject exceeds predetermined boundaries, such as entering an off-limits room, or walking beyond a certain radius from the facility, the system can tailor a page or other alert to the appropriate party, i.e., a caregiver. In such an instance, a caregiver can check a network terminal or other device to learn the subject's exact location. A caregiver in one location can thereby respond instantaneously to any of a plurality of ambulatory subjects. The system maintains continuous monitoring as subjects move freely throughout the space. Subjects also feel a sense of freedom, moving about the area ad libitum and unaccompanied, without reducing personal safety. This sense of freedom adds to the goals of the system.

Direct monitoring of a subject is accomplished by a physiological monitoring subsystem 130 and a cognitive monitoring subsystem 140. Each of these subsystems includes at least one sensor coupled to the networked computer. Preferably, a number of sensors are distributed throughout the area in which the subject can move, such that the chronological gap between any two consecutive parameter samplings is minimized, regardless of the location of the subject within the area.

Input in the form of data signals is received from the sensors and from remote network nodes. Both the sensors and the remote nodes are distributed throughout the defined multi-room space. For each sensor, a coupled signal generator generates a digital signal corresponding to the obtained measurement. The signal is then transmitted to the networked computer, associated with a SIC, and then stored and analyzed.

The tracking subsystem 120 makes possible the use of promiscuous sensors, which measure parameters without regard for the identity of the monitored subject. By reviewing subject identities and locations from the tracking subsystem, the system can determine the identity of the subject sufficiently proximate to the signaling sensor for measurement to be achieved. That subject's Subject Identity Code (SIC) is then associated with the parameter measurement signal from the sensor.

According to some embodiments of the invention, the system may be configured so that users of the system may access data records stored in the data storage device 104 through one of the remote nodes 108. By entering control inputs at the remote nodes 108, the user may also specify how the stored data records are to be displayed. For example, the system may display the data record on a view-screen or the data record may be printed.

According to some embodiments of the invention, the full data record is not available to all users of the system, but rather a modified data record may be made available to a user. The content of the modified data record is dependent upon the access level of the user.

For illustration purposes only, and not for purposes of limitation, a user of the system may include a subject's doctor, the subject's family member, the subject's caregiver, a system administrator, a researcher, or the subject himself or herself. There may be an access level associated with each of these different system users, the access level specifying how much or which portions of the complete data record may be displayed or accessed by the system user. The subject's doctor or caregiver will preferably have more access to the full data record for each subject then members of the subject's family.

Based upon the system user's access level, a data filter which forms part of the computer 102 may tailor the modified data record so that the information in the modified data record is appropriate for the access level of the system user. The delivery of this information may be further modified to reinforce the culture, values and needs of the organization and subjects so that all stakeholders are working together with a common purpose.

The data filter may also add selected data to the data record from third party sources, the data from the third party sources selected to educate or inform the system user. For example, if a particular subject was diagnosed as having a sleep disorder, a family member of the subject may see a modified data record where additional information regarding the sleep disorder is presented for the family member's education. In contrast, the corresponding modified data record that is made available to the subject's doctor may not require this additional information.

Figure 2:
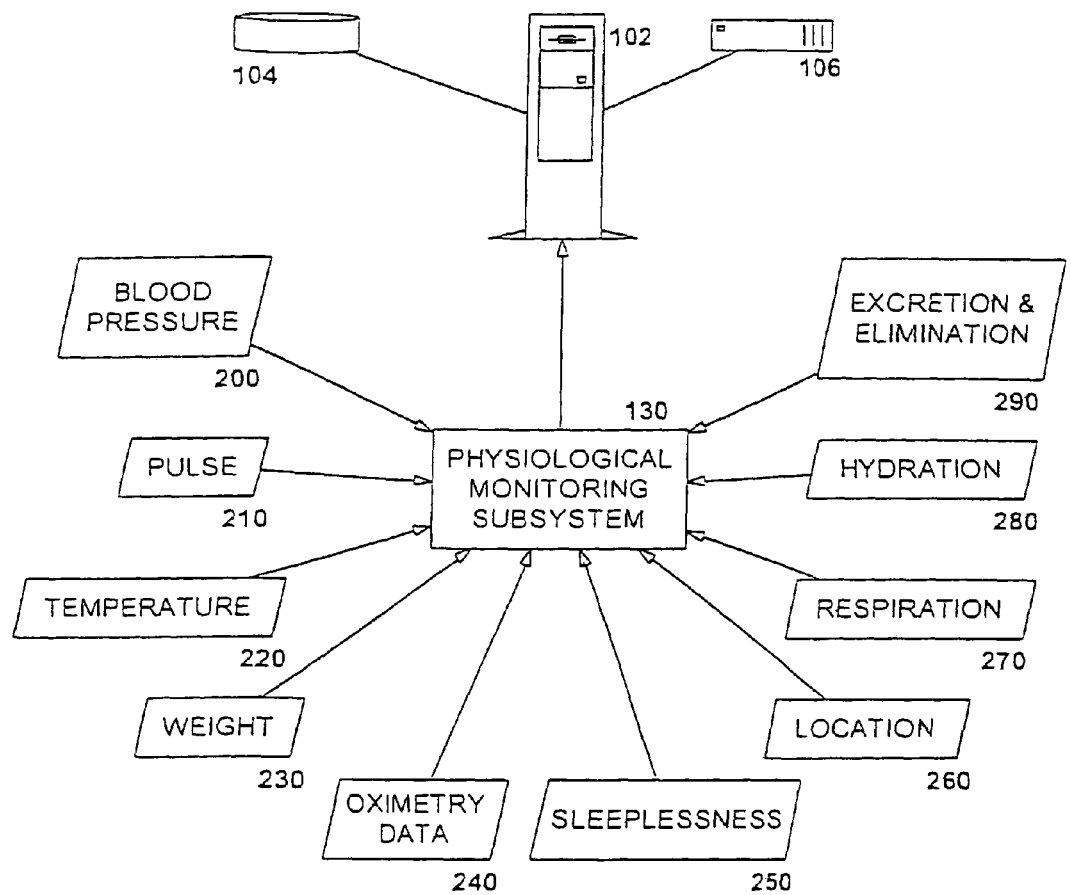
FIG. 2 is a block diagram that further illustrates the physiological monitoring subsystem of the system illustrated in FIG. 1.

FIG. 2 is a block diagram that further illustrates the physiological monitoring subsystem 130 of the system of FIG. 1.

Referring to FIG. 2, the physiological monitoring subsystem 130 includes sensors to measure vital signs and other health parameters of a subject. These parameters preferably include blood pressure 200, pulse 210, temperature 220, weight 230, oximetry data 240, sleeplessness 250, subject location 260, respiration rate 270, body hydration 280, and excretion/elimination data 290. Other embodiments of the invention may measure more or fewer parameters than those shown in FIG. 2.

A subset of the sensors measures parameters with the active collaboration of the subject. These sensors comprise a cuff to measure blood pressure 200, an oximetry 240 device, a respiration monitor 270 and a remote node 108, preferably a computer terminal, where the subject can enter subjective inputs. A person skilled in the art will also recognize other sensors which can measure parameters with the active consent and participation of the subject.

Collaborative sensors can be stationary devices; alternatively, a telemetric sensor can be worn by the subject and the data transmitted from it to a proximate receiver. Distribution of receivers throughout the defined space permits the subject to move with uninterrupted data acquisition and transmission by the system.

The care giver can also inquire the subject on a routine bases with a series of mental, emotional, and/or physical tests (get up and go, grip strength etc.) that are inputted into a remote terminal, and which become part of the overall data base that can be mined for changes in condition and relayed to the appropriate party in a tailored format.

In contrast to the subset of sensors discussed above, a second subset of the system's sensors may obtain parameter measurements irrespective of subject cooperation. More specifically, those sensors are operative to measure physiological or cognitive parameters as the subject engages in everyday activities that are generally unrelated to health monitoring. These sensors may be of many types, including thermocouples, infrared and motion sensors, conductive elements, force sensors and other transducing sensors. A person skilled in the art will also recognize other sensors that can be used.

As an example, a load sensor can be embedded in a chair in the subject's personal living space, enabling body weight 230 to be measured whenever the subject sits in the chair. In this manner, the subject need not use a conventional scale, consciously report the weight reading, or even be aware that the load sensor resides in the chair. The unrelated act of sitting in the chair, e.g., to rest, read or watch television, is sufficient to enable the system to obtain a body weight measurement.

Weight 230 may be detected via force sensors positioned to measure z-axis force applications to the subject's sleeping surface. These sensors thus enable determination of the mass of an object or person resting on the surface. Sleeplessness 250 may be simultaneously measured using additional sensors to detect lateral motion of the surface owing to movement of the subject. Lateral motion of the subject during the night is often indicative of subject restlessness and can be utilized to perceive and quantify sleep difficulties or disorders.

Temperature 220 and body hydration 280 may be measured by thermocouples embedded in a toilet seat. A set of conductive elements may measure body impedance during a routine toileting event. From this impedance data, both pulse and body hydration can be calculated. These calculations are well-known in the art.

Bowel movement and urination 290 may be monitored by sensors in the toilet seat and bowl. Thermocouples in the seat and bowl measure the subject temperature 220 and the temperature of the bowl contents, respectively. As well, force sensors provide weight 230 readings at the beginning and end of the toileting event. Changes, occurring during the toileting event, in subject weight and in the temperature of the bowl contents can be used to calculate the fecal mass and/or urine volume of the event. The data also displays the subject's regularity in terms of frequency and volume. When accumulated over time, this information is useful to detect changes in the subject's habits or abilities. These changes can be due to physical problems or to declining mental faculties.

Similarly, force sensors, e.g., load cells, may be employed elsewhere to detect the subject's weight 230. Force sensors are deployed under the legs of the subject's bed, in the feet or casters of a chair in the subject's living space, or in a toilet seat/footpad arrangement. Body mass is appreciated when the subject rests on the article in which the force sensors have been inserted.

Temperature 220 may also be monitored with a thermal (infrared) camera, which scans a part of the subject's body such as the forehead. This scan can occur while the subject is engaging in any routine activity, i.e., applying makeup in front of a mirror, using a computer terminal, or other activity in which the subject's head is predicted to be within the defined zone of sensor measurement. From this scan, the system determines the relative body temperature without physically contacting the subject or interfering with the subject's normal activities.

Figure 3:
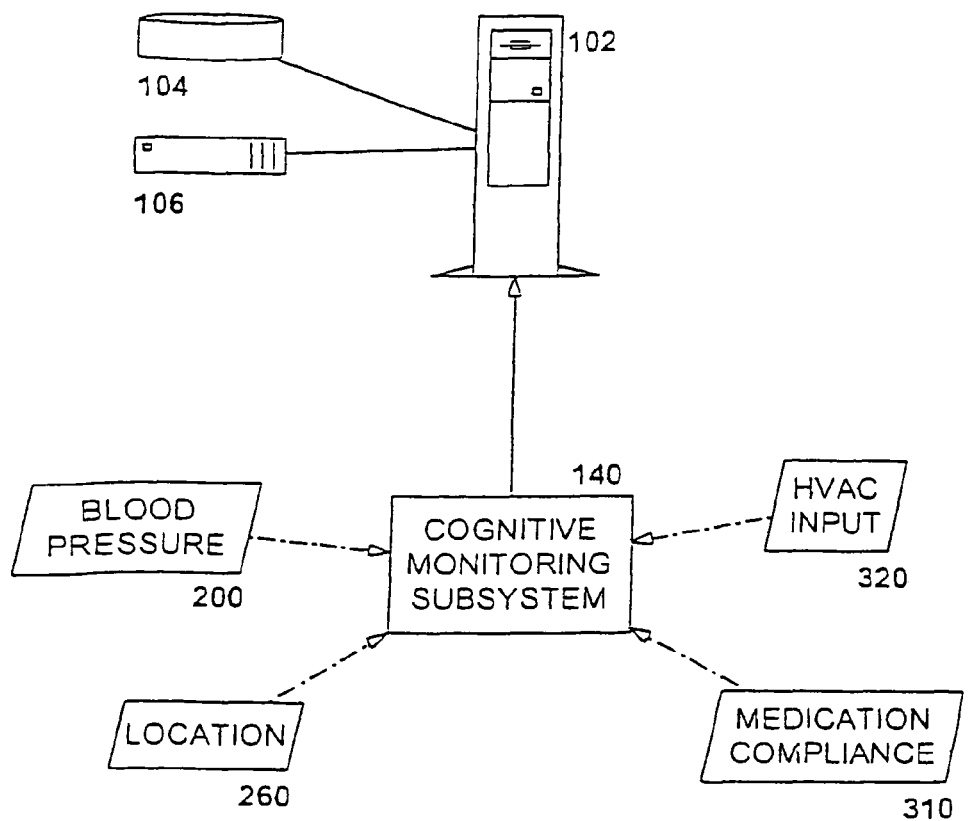
FIG. 3 is a block diagram that further illustrates the cognitive monitoring subsystem of the system illustrated in FIG. 1.

FIG. 3 is a block diagram that further illustrates the cognitive monitoring subsystem 140 of the system of FIG. 1. The cognitive monitoring subsystem 140 is operable to measure indices of the mental health of a subject. This health is specifically focused on the awareness, perception, reasoning, memory and judgment of the subject.

As shown in FIG. 3, the measured indices preferably include blood pressure 200, location 260, medication compliance 310, and Heating, Ventilation, and Air Conditioning (HVAC) input 320. Other embodiments of the invention may measure more or fewer indices than those shown in FIG. 3.

According to some embodiments of the invention, cognitive parameters are measured primarily passively and without subject cooperation. According to some embodiments of the invention, some indicia of mental health may be derived from interactive behavior that is otherwise unrelated to the measuring of a cognitive parameter.

An example of the direct measurement of a cognitive parameter is observation of medication compliance 310. Data is generated from a medication compliance device that is provided to each self-medicating subject. The device includes a sensor to record opening and closing of the medicine cabinet door. Load cells are positioned beneath each medicine container and are operative to record the mass of a container and its contents. By controlling the size or shape of the containers, each container can be uniquely and consistently identified. The load cells are sufficiently discriminating to discern when a pill or tablet has been removed from a container, indicating that the patient has removed medication corresponding to that container.

An incremental decline in medication compliance can be illustrative of declining mental faculties. By recording compliance over a significant period of time, this slow deterioration in compliance can be noted by a caregiver or other health professional.

Cognitive indicia may be indirectly obtained by evaluating irregularities in subject behavior. Sudden changes in adjustment of environmental controls or lighting 320 can also signify aberrant behavior. Failure to submit to routine, interactive parameter measurements, such as blood pressure 200, are detected from the data generated by the physiological monitoring subsystem 130.

By the same token, eccentric movement, wandering and improper attempts to enter personal living spaces of another subject are indicative of forgetfulness and confusion. The system can analyze mobility data 260 to determine instances wherein the subject mistakenly tried to enter another subject's room, wandered or repeatedly visited the toilet when not necessary. By tracking mobility over time, a health professional can assess discrete wanderings in the context of the subject's normal routine, as established over a period of time. Declines in cognitive ability are thereby more readily appreciated.

The invention may be practiced in many ways. What follows are exemplary, non-limiting descriptions of some embodiments of the invention.

According to embodiments of the invention, a data delivery system is set up so that it can also acquire necessary information via the internet or manual data input so as to give to the receiving party the best possible picture of what is happening and tailor that information to the individual receiver so as to best accomplish the goals of the system.

The subject is empowered to disable data acquisition relating to one or more parameters, by deactivation of either a sensor in the subject's personal living space or of the subject's unique transmitter. In the latter instance, the system is not stopped from acquiring the measurement; the system is simply unable to associate a SIC with the value.

Deactivation by a subject of data collection for that subject may be inadvertent. Conversely, the subject can feel the need for greater personal privacy, whether generally or to engage in an activity having the potential to trigger an alert. While the subject is free to disable data collection, the deactivation event itself is duly recorded. Such events are noteworthy, as they can indicate a change in mental health status or an intentional obstruction of proper system operation.

Redundancy is employed to maintain a continuous stream of data, even in the face of changes in the subject's daily routine. Using body temperature as an example, thermocouples are embedded in the subject's toilet seat as described. The thermal camera acquires temperature data in a different location. Thermocouples are also embedded in other everyday objects in still other locations. Because sensors are embedded within everyday objects, the sensor cannot obtain measurements when the article in which it is embedded breaks or is otherwise out of service. By using a plurality of sensors to measure a single parameter, that parameter can be constantly monitored even if, for example, a specific wall-mounted sensor fails or the subject's toilet becomes temporarily unusable.

The passive acquisition of physiological and behavioral measurements ensures greater compliance with data measurement and recordation than occurs in traditional residential care procedures. Long-term record-keeping permits a current measurement to be viewed in the context of the patient's individual history for the given parameter. This "institutional memory" improves evaluation of the subject's health status.

Deviations from the subject's normal values are also more rapidly brought to the attention of an appropriate party, e.g., health care provider, on-site caregiver, subject or other entity authorized to access the data. Lastly, the subject's daily activity and routine are impacted much less than in traditional residential care facilities, where a patient must regularly submit to a caregiver's measuring of parameters, i.e., temperature or pulse.

The sensors in the system may be coupled to the network via a wired or wireless connection. Data transmission of signals to the data storage device is thereby enabled without regard for the type of sensor or coupling means for that particular sensor.

The system may use a variety of audible and visual cues to prompt subject behavior and compliance. For example, a simple chime or other tone can be employed to signal meals. As a more relevant example to health and elder care, a colored or flashing light in the subject's medicine cabinet can be used to signal medication intake. A tone, synthesized voice or email message can be employed to signal the need for a parameter to be interactively measured. The system can turn on the subject's room lights during the night to wake the subject and prompt a toilet visit to maintain continence it can chose to use red lights instead of white lights so as to alert but not to waken. A tone can also be used both to signal when a subject nears the limits of the monitored area and as a more general warning that the subject is about to leave the facility grounds. As is well-known with wireless paging technology, a vibration or silent mode alert can be employed to provide the subject a greater level of privacy. A person skilled in the art will also recognize other cues that can be used.

According to some embodiments of the invention, the output of the system may include summaries and request responses for each monitored subject. The outputs are tailored for each receiving party (e.g., subject, physician, caregiver, or subject's family member). Reports provide detail on subject health over each reporting period. Data in these reports may include the care services that were provided to the subject, described by frequency, type, and cost; types of activities in which the subject participated (again, by frequency and type); and a movement report. These summaries provide specific health information and also convey a more general representation of the subject's quality of life and care in the facility. The tailored response also educates each person receiving the information to better understand their particular role in the overall system and act accordingly.

Thus, according to embodiments of the invention, caregivers and administrative personnel are relieved of the task of relating this information to physicians, family members, and others. Thus freed from performing a number of administrative duties, caregivers can devote a greater portion of their time to providing care and service to their subjects. The stress between members of the community is further reduced because everyone is educated and reminded of their role in delivering of services that will affect the quality of life for the resident.

According to some embodiments of the invention, subject data may be remotely accessed to by health professional, family members, or other authorized persons that are geographically separated from the caregiving facility, aiding in the sharing of subjective and objective measurements. The subject data may be transmitted in a user-friendly format through digital channels.

According to some embodiments of the invention, remote access is through a network connection that is password protected, encrypted, and tailored to each individual user depending on their predetermined access level. Information may be presented in such a way as to further the goals and objectives of the system. The subject may control access and the degree of viewable information for each party that desires to view subject data. Subject data privacy is thereby assured with respect to each type of viewer, i.e., physician, family member or other person permitted to view such information.

It should be apparent that embodiments of the invention may work effectively with subjects in various states of health. While embodiments may be most efficacious when applied to fully ambulatory subjects in a health care facility, the embodiments may also be adapted to monitor subjects that require ambulatory assistance or subjects that live alone and that depend on community-based care.

Another aspect of the present invention is a method of monitoring indicia of the health status of a subject. Monitoring is performed in a predominantly passive manner, without the cooperation of the monitored subject.

In long term care facilities, deviations from the standard parameter values are significant and receive the attention of a caregiver or health care provider. As discussed, caregiver turnover reduces the familiarity of any one caregiver with the broad history of a particular patient or the culture that the patient is use to. The system of the present invention improves patient care by serving as the "institution", compiling and retaining a detailed history of all of the pertinent health parameter measurements of a subject as well as social aspects that allow the patient to feel at ease and comfortable through consistency and routine that the system reinforces.

A corollary feature of this role is to sooner detect small or frequent changes in data patterns. By compiling a large body of information describing a subject's health history in terms of certain parameters, the system readily detects variations in data patterns as they occur. The system can thereby immediately alert the proper party of the deviation. To accomplish this goal, data is logged and analyzed for comparison with pre-established limits or averages complied by the computer over a period of time. When the parameter measurement falls outside the pre-approved range of values or averages, a tailored notification is issued to the appropriate party for remedial action.

Prior to and during move-in to the facility, subjects may be asked to complete different profiles, summarizing financial, health, habits, likes, dislikes, personal and historical information. These assessments and information may be stored by the system and can be added to at any time through the internet.

The health assessment will be the basis for a health care service plan. The system profile establishes health parameters and negotiated risk agreements, described in greater detail below. The personal assessment is a list of several hundred questions that subjects complete to help staff quickly find commonalities with other subjects and staff, these persons having also completed the profile assessment. The profiles are maintained in a database in the system's data storage device, when the system then is called on to deliver information it can use these profiles to tailor that information to the person receiving it. The information can also be queried by caregivers, administrators and other authorized parties.

Embodiments of the invention permit the establishment of dynamic parameters in three categories of subject health: vital signs, inputs/outputs, and behavior and cognitive indices. These parameters are individualized and explicit. They are formalized in a negotiated-risk agreement executed by the subject, physician, family, and caregiver. Negotiation by these parties of parameters gives subjects levels of independence and risk-taking ability that neither affect facility liability exposure nor jeopardize the personal safety of the subject. The parameters can be amended from time to time, according to changes in a subject's cognitive and/or physical capabilities.

This negotiation also determines whom to notify when any one of a number of events occurs. One such event is a subject parameter exceeding the predetermined threshold. Alternatively, a number or particular group of parameters can be out of compliance before an alert is warranted. In another example prompting an alert, a subject parameter can show a large percentage change from one measurement to the next. By tracking movement in parallel with other parameters, the system can discern when a pulse or temperature increase is due to heightened activity rather than the result of a health aberration.

This negotiation also allows for the system's tailored responses to reinforce the agreements and goals that are agreed to.

The method comprises providing a networked monitoring system, as described above.

Generally, a plurality of detectors are positioned within the defined space, each of the plurality of detectors capable of detecting a physiological parameter of the subject. Examples of physiological parameters have been previously described and include, for example, pulse 210 or weight 230.

Parameter values are then passively measured, without subject cooperation or active participation in the measurement step. A signal corresponding to the measured parameter value is generated and transmitted to the data storage device. The measured parameter value is associated with a subject identifier and, where applicable, a chronological identifier. In taking these initial parameter measurements, the system thereby establishes a baseline value for each health component. Taken in tandem with the parameter limits established at the outset, the baseline constitutes the standard against which the system evaluates subsequent measurements.

Subsequent parameter trending establishes an ongoing history of the subject's physical and mental health, as well as providing a context in which to evaluate current measurements. Specifically, normal trends can be identified for each subject and parameter. In this way, normal fluctuations are more readily recognized and distinguished from abnormalities requiring health care attention.

This institutional memory provides a fuller record of objective and subjective observations regarding the subject. Against this tapestry, subtle deviations in vital signs, daily routine and cognitive performance are more accurately assessed and more promptly detected.

Occurrences calling for party signaling include instantaneous conduct-oriented events such as "panic" or emergency calls by subject or facility staff, disabling of one or more sensors by a subject, or deviations in one or more monitored health parameters.

Variations in parameter values are noted as they occur, with alerts generated according to response criteria defined by a system operator. The system permits the assignment of priorities to the various parameters, as well as to the degree of deviation necessary before an alert will be generated and sent.

For less critical parameters, variations are merely noted. On the other hand, detection of a medically significant parameter aberration can be set to prompt an immediate notification event. Upon receiving an emergency call from a subject's personal transmitter-signifying that immediate attention is required-the system responds with appropriate cues to garner the attention of the proper party, including light, sound and pager signals.

The patient monitoring and tracking system and method of the present invention use real-time data collection and digital communication to improve the health care and quality of life of subjects in nursing homes, assisted living facilities, residential care facilities, adult foster care homes, and private residences serviced by community-based care. The present invention is uniquely adapted to these care settings. It develops, adapts, and integrates thermal infrared monitoring, sonic recognition, radio frequency transmitters and other technologies. These technologies are combined with Internet-based information and communication networks to monitor human health and provide behavioral cues to prolong subject independence. The monitoring system according to the present invention gathers, logs, and transmits health-related data such as body temperature, oximetry, pulse, weight, hydration, blood pressure and mobility, doing so without interfering with subjects' normal activities or home environment. Ambient sensors control the heating, ventilation and air conditioning (HVAC) to suit subject needs.

The present invention differs from the traditional model of long-term care by reducing the amount of risk faced by facilities, thereby freeing them to fully experiment with and realize the potential of a subject-centered care model. In effect, the present invention shifts the paradigm of care back several generations, recalling a time when family members, country doctors, and others were closely in tune with an elderly person's history, condition, habits and preferences and acted with a common purpose.

By being able to tailor each individual response to the appropriate party in a manner that reinforces the social as well as health objectives the patients are cocooned in a stable and predictable environment thus relieving many of the anxieties that present systems create. Just as the system can analyze the condition of an individual and look for changes of condition the system can aggregate all of the information collected and look for subtle changes in the condition of the organization using the same basic techniques. This allows for the management to leverage itself by inputting its own baselines regarding acceptable changes in the aggregated numbers and alert the appropriate party with a tailored response.

An example of this could be response times to alert calls, or the average weight of the subjects, a small decline might mean a problem with the food service. The system and data are the same, it is just the baselines or averages that are adjusted from individual to group as the health of the facility is measured.

Embodiments of the invention address the needs of at least six groups: subjects receiving health care; caregivers and care-giving facilities; the subject's families; physicians; researchers and management. These groups presently do without important, reliably consistently and routinely-gathered health and quality indicating information in most settings. As a result, personnel caring for an elderly person living alone or in a large facility are often unable to proactively diagnose and treat illnesses, tend to their changing conditions or address their needs in a socially and consistent way.

Moreover, conventional scenarios frequently limit the time and attention given to any one subject. As well, staffing patterns in these settings—and the nature of operation of such institutions—often limit a resident subject's autonomy. Home health aides must visit several patients each day, restricting the amount of time devoted to data acquisition at any one site. Residential facility caregivers cannot monitor a large plurality of subjects simultaneously. The system automatically records important physical and mental health indicators.

Caregivers, freed from paperwork needed to meet accounting, insurance, and legal requirements, can spend more time with subjects delivering consistent services because the information received is tailored to their needs. Health care personnel also gain a better understanding of subject health trends and can engage in meaningful conversations about the type of care provided. Staff can manually enter observations and other comments about a subject's daily life into the computer via touch screens and other technology found throughout the facility. Managers can be sure that care plans are followed and the quality of care is consistent with the goals of the system.

The system can facilitate proper behavior by all interested parties by tailoring the information and content to further the health, behavior and environmental goals of the system.

Logistic concerns and legibility issues are thereby reduced. Automated records also simplify billing and minimize problems associated with high caregiver turnover rates. Administrative practices are thereby substantially automated. As well, the care facility can receive subject feedback regarding quality of services, care giving and physical resources. Subject comments, entered into the system, can be employed to improve the quality and efficiency of the facility. Thus, the system can measure the health of an individual as well as deliver subjective feedback regarding the individual's assessment of the quality of services delivered by the system.

In an elder care setting, embodiments of the invention grants subjects more control over their daily decisions without sacrificing their safety. Subjects have freedom to take risks which otherwise would be prohibited. Historical data recorded by the system gives subjects the ability to make informed choices about the type of care they receive. Dynamic risk-autonomy health parameters and custom health summaries give subjects incentives to improve their mental and physical well-being, thereby prolonging life and reducing health care costs. Prompts prolong subject independence as cognitive ability changes.

The facilities can reinforce their culture with little risk that a different manager or staff will change the system and create anxiety for the patients because the information is tailored to the particular staff member in such a way as to reinforce consistency and routine. For the families of monitored subjects, family members can be informed as to the specific types, quantity and subject-perceived quality of health care services provided to the subject. Families receiving health summaries and billing breakdowns based on the information collected by the computer. Families need not rely solely on generic billing statements and the written notes of caregivers. The billing statements can include subject comments concerning quality of health care services, caregivers and the facility's physical resources, informing families thereon in substantially real-time. In addition, family members can be advised automatically of emergencies via real-time system-initiated data transfer over the Internet, via telephone or pager or access the information over the internet through a private portal.

Doctors and other authorized persons needing detailed records on subject health have immediate access to necessary data via e-mail and the Internet. Trends for subject vital signs; system inputs and outputs; subject movement; frequency, variety and duration of activities; and other crucial information are accessed easily through the system computer. Physicians do not have to rely on written logs that are often maintained at the facility and frequently difficult to interpret. With a clearer understanding of health trends, physicians and others can prescribe treatment plans based on historical data. Computer-based alerts and records also speed response time.

Using system-recorded data, researchers can quantitatively judge the success of experimental intervention strategies that have been implemented at the subject's facility. As well, governmental agencies can measure quality of care in regulated facilities. The spatial monitoring component of the system can be especially useful for research addressing the influence of facility design on behavior.

As an example and not by way of limitation, an electronic scale having an embedded transmitter can be provided in a subject's living space. When the subject stands upon the scale, the measurement is transmitted by the scale to the networked computer for chronological identifier association. The scale can be hard-wired to the network or its location in the room can be fixed.

The system receives data from the spatial monitoring apparatus to indicate that Subject A is located in the rest room of Subject A's personal living space. Combining these data into a data record, the system can thereby determine that the scale sensors are weighing Subject A. This determination can be accurately made even if another monitored subject is contemporaneously present in Subject A's living space. By triangulating data received from the unique personal transmitter devices of the spatial monitoring apparatus, the system can discern that Subject A is located in the area of the room where the scale is also located. Minor variations in subject parameters can be set to be recorded but not trigger alerts. For example, day-to-day fluctuations in body weight are normal, due to water retention, variations in meal size or heavier attire. If weight continues to fluctuate or continues in a relatively steady trend, an alert can then be transmitted to a health professional that the subject is gaining or losing weight, as the case may be.

In contrast, an elevation in a subject's body temperature is a less normal occurrence and is generally significant enough to warrant caregiver notification or attention. As described, the system can discriminate between health-related parameter departures and normal deviations flowing from everyday activities, such as exercise or other strenuous physical activity.

Similarly, detection of an increase in subject pulse rate can be set to cause the system to transmit a warning to a caregiver. However, an alert will not be generated when the pulse anomaly occurs during the time of day in which the subject exercises. Acting dynamically, the system discriminates between recurring exercise periods and isolated instances of strenuous activity.

The system can also monitor activities to detect temporal discrepancies in subject routine. For example, a subject who becomes violently ill might make several bathroom visits in a short time period. While the first visit violates no parameter boundary, the system detects the repetitive visits. Because of both the predetermined parameter settings and baseline data, the system detects a physical or behavioral irregularity—multiple trips to the rest room in an abnormally short period of time—and signals an appropriate party for investigation or other response.

An integrated subject monitoring system facilitates measurement, collection and analysis of data pertaining to the health status of a subject and the delivery of that information tailored to each individual user taking into account culture, cognition and location. The system includes a network-coupled computer and subsystems monitoring subject location within a defined space and the curtilage thereof and obtaining measurements of a subject's physiological or behavioral/cognitive parameters within the defined space. Parameter data is obtained primarily passively, without the cooperation or active participation of the subject and is combined with data collected through searching other databases and manual input.

A method of monitoring the physiological and behavioral/cognitive health status of an ambulatory subject involves monitoring in a primarily passive fashion, irrespective of the active collaboration of the subject. Subject health indicia parameters are continuously monitored, sampled and recorded. Captured values are compared to initial baseline values established for each of the measured parameters as well as to the trend for the parameter of that subject. Readings falling outside the boundaries trigger a signal to be sent to an appropriate party in a deliberate format that reinforces the overall outcome desired by the system.

A person skilled in the art will be able to practice the invention in view of the present description, where numerous details have been set forth in order to provide a more thorough understanding of the invention. In other instances, well-known features have not been described in detail in order not to obscure unnecessarily the invention.

Having described and illustrated the principles of the invention in various embodiments thereof, it should be apparent that the invention can be modified in arrangement and detail without departing from such principles. All modifications and variations are claimed that fall within the spirit and scope of the attached claims.

The invention claimed is:

1. A system for monitoring health parameters of subjects, the system comprising:
   a physiological monitoring subsystem that measures physiological parameters of the subjects and transmits first data corresponding to the measured physiological parameters;
   a behavioral and cognitive monitoring subsystem that measures behavioral and cognitive parameters of the subjects and transmits second data corresponding to the measured behavioral and cognitive parameters;
   a tracking subsystem that monitors tracking signals transmitted from tracking transmitters and transmits third data corresponding to an identity and a location of a corresponding one of the subjects, each of the tracking transmitters associated with a the corresponding one of the subjects;
   the tracking subsystem, the physiological monitoring subsystem and the behavioral and cognitive monitoring subsystem each including a plurality of sensors distributed throughout an area where the subject can move;
   a computer that receives the first data, the second data, and the third data, the computer including:
      a processor that analyzes the first, second, and third data and generates a data record based upon the analysis, the processor associating the first and second data from the distributed sensors of physiologic monitoring subsystem and the behavioral and cognitive subsystem with the third data for the corresponding one of the subjects based on proximity to nearest distributed sensors, and
      a data storage device that stores the data record for the corresponding one of the subjects;
   the data record corresponding to one of the subjects further including fourth data corresponding to the one of the subjects from third party sources;
   a remote node that communicates with the computer, that outputs a modified data record to a user of the system, and that accepts control inputs from the user; and
   the processor further including a filter that tailors the modified data record to a predefined access level of the user based on a relationship of the user to the subject.

2. The system of claim 1, in which the remote node communicates with the computer through a network.

3. The system of claim 1, the computer programmed to transmit data to the remote node in real-time.

4. The system of claim 3, the computer programmed to transmit data to the remote node automatically when an emergency situation is detected.

5. The system of claim 1, the computer programmed to automatically transmit an alert message when an emergency situation is detected.

6. The system of claim 1 in which multiple users have access to the system via the remote node, the users including a caregiver, a family member of the subject and a physician, each user having an access level pertinent to their role in relation to the subject, the filter tailoring the modified record according to the role of the user.

7. The system of claim 1 in which the multiple users each can enter fourth data comprising observations about each subject.

8. The system of claim 1, in which the subject can disable data acquisition relating to one or more parameters.

9. The system of claim 1, in which the subject can control user access to the modified data record.

10. The system of claim 1, in which the subject can enter subjective data in the remote node.

11. A system for monitoring health parameters of a subject, the system comprising:
   a computer including:
      a processor that analyzes first data corresponding to measured physiological parameters of the subject, second data corresponding to measured behavioral and cognitive parameters of the subject, third data corresponding to an identity of the subject and a location of the subject, fourth data corresponding to the one of the subjects from third party sources; fifth data corresponding to billing records to the one of the subjects; and that generates a data record based upon the analysis of the first, second, third, fourth, and fifth data, and a data storage device that stores the data record for the subject;

a physiological monitoring subsystem external to the computer that measures physiological parameters of the subject, that generates the first data, and that transmits the first data to the computer;

a behavioral and cognitive monitoring subsystem external to the computer that measures behavioral and cognitive parameters of the subject, that generates the second data, and that transmits the second data to the computer;

a tracking transmitter that is wearable by the subject;

a tracking subsystem external to the computer that receives tracking signals transmitted from the tracking transmitter, that generates third data, and that transmits the third data to the computer;

the tracking subsystem, the physiological monitoring subsystem and the behavioral and cognitive monitoring subsystem each including a plurality of sensors distributed throughout an area where the subject can move;

a remote node that communicates with the computer, that outputs a modified data record to a user of the system, and that accepts control inputs from the user;

the processor associating the first and second data from the distributed sensors of physiologic monitoring subsystem and the behavioral and cognitive subsystem with the third data for the subject based on proximity to nearest distributed sensors; and the processor further including a filter that tailors the modified data record to a predefined access level of the user based on a relationship of the user to the subject.

12. The system of claim 11 in which multiple users have access to the system via the remote node, the users including a caregiver, a family member of the subject and a physician, each user having an access level pertinent to their role in relation to the subject, the filter tailoring the modified record according to the role of the user.

13. The system of claim 11 in which the multiple users each can enter fourth data comprising observations about each subject.

14. The system of claim 11, in which the subject can disable data acquisition relating to one or more parameters.

15. The system of claim 11, in which the subject can control user access to the modified data record.

16. The system of claim 11, in which the subject can enter subjective data in the remote node.

* * * * *